United States Patent
Abe et al.

(10) Patent No.: US 7,123,288 B2
(45) Date of Patent: Oct. 17, 2006

(54) ELECTRONIC ENDOSCOPE ELIMINATING INFLUENCE OF LIGHT DISTRIBUTION IN OPTICAL ZOOMING

(75) Inventors: Kazunori Abe, Saitama (JP); Mitsuru Higuchi, Saitama (JP); Daisuke Ayame, Saitama (JP); Shinji Takeuchi, Saitama (JP)

(73) Assignee: Fujinon Corporation, Saitama (JP)

( * ) Notice: Subject to any disclaimer, the term of this patent is extended or adjusted under 35 U.S.C. 154(b) by 626 days.

(21) Appl. No.: 10/259,282

(22) Filed: Sep. 27, 2002

(65) Prior Publication Data

US 2003/0063398 A1 Apr. 3, 2003

(30) Foreign Application Priority Data

| Sep. 28, 2001 | (JP) | ............................. 2001-299226 |
| Sep. 28, 2001 | (JP) | ............................. 2001-299227 |
| Sep. 28, 2001 | (JP) | ............................. 2001-301804 |

(51) Int. Cl.
*H04N 7/18* (2006.01)
(52) U.S. Cl. .......................................... 348/65; 348/68
(58) Field of Classification Search ............. 348/65–76
See application file for complete search history.

(56) References Cited

U.S. PATENT DOCUMENTS 4,953,937 A * 9/1990 Kikuchi et al. ............... 385/33

| 5,339,159 A | * | 8/1994 | Nakamura et al. ............. 348/71 |
| 5,582,576 A | * | 12/1996 | Hori et al. .................. 600/167 |
| 2002/0147383 A1 | * | 10/2002 | Weber et al. ................ 600/109 |

FOREIGN PATENT DOCUMENTS

| JP | 01-223932 | 9/1989 |
| JP | 2000-037345 | 2/2000 |

* cited by examiner

*Primary Examiner*—Andy Rao
(74) *Attorney, Agent, or Firm*—Snider & Associates; Ronald R. Snider

(57) ABSTRACT

The invention provides an endoscope having a scope that takes an image enlarged by driving a movable lens of an optical zoom mechanism by a CCD and displays an image of an object to be observed, wherein a multiplier multiplies RGB color signals by a coefficient set in view of light distribution of illumination light depending on focusing distances of the movable lens, thus eliminating uneven brightness resulting from varying light distribution depending on the focusing distances in enlargement photography. A red component cut filter for cutting a long wavelength side in a red band of the illumination light is provided in a light source unit to improve redness. Further, a coefficient for averaging a brightness signal for a predetermined number of pixels for each horizontal line is calculated, and this coefficient calculation may eliminate unevenness.

8 Claims, 11 Drawing Sheets

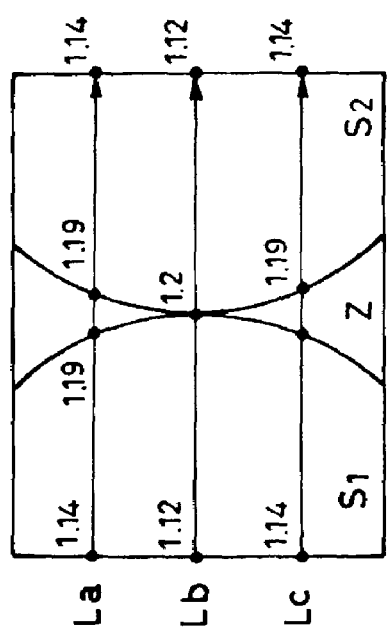
FIG. 4 (A) DISTANCE D1
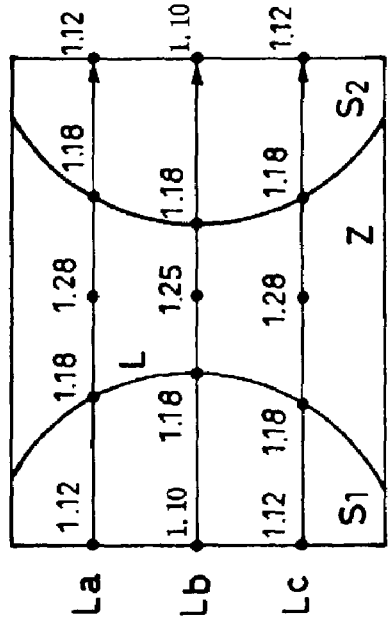
FIG. 4 (B) DISTANCE D2
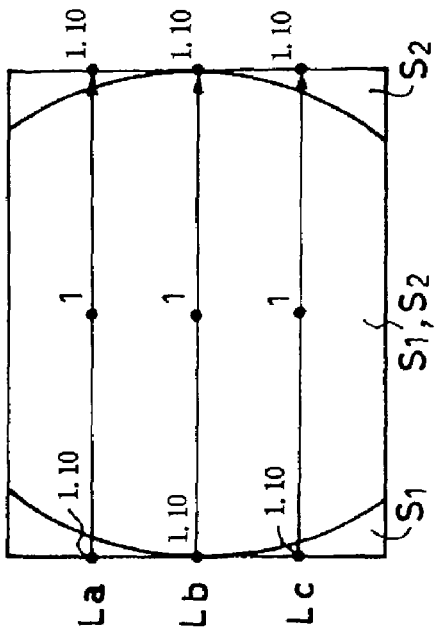
FIG. 4 (C) DISTANCE D3
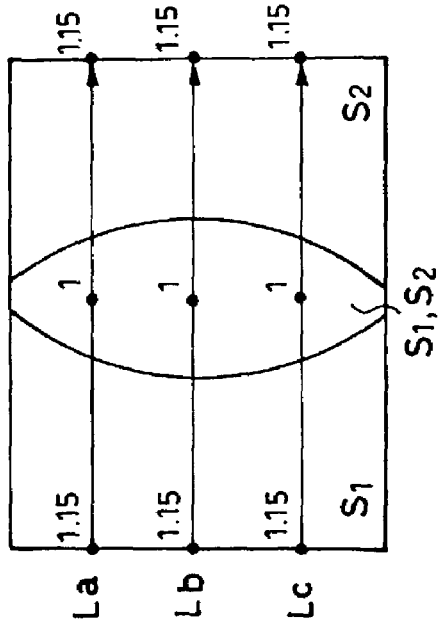
FIG. 4 (D) DISTANCE Dn

FIG. 9
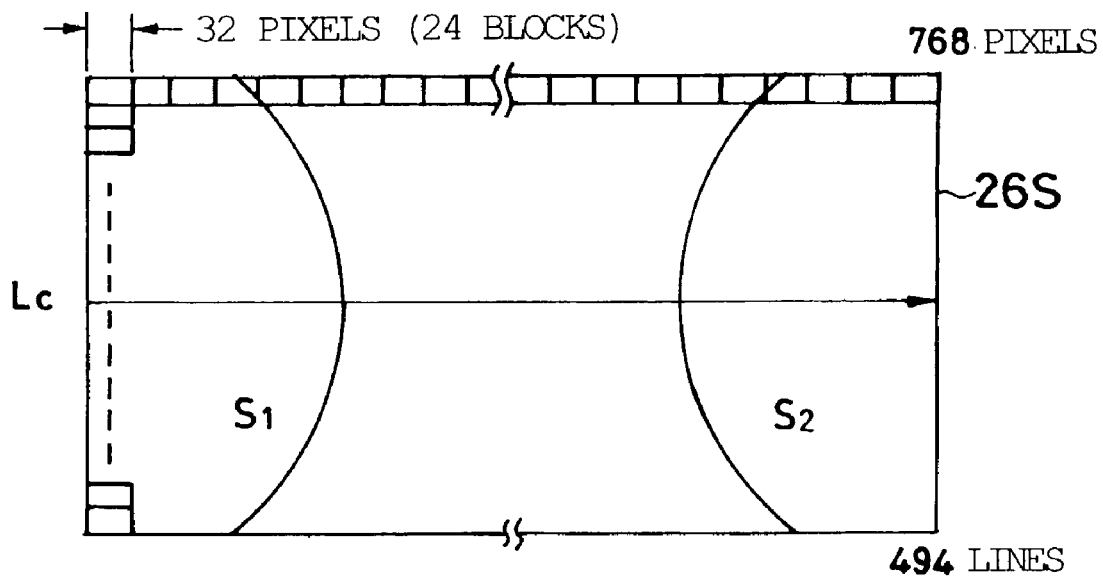
FIG. 10 (A) AVERAGE
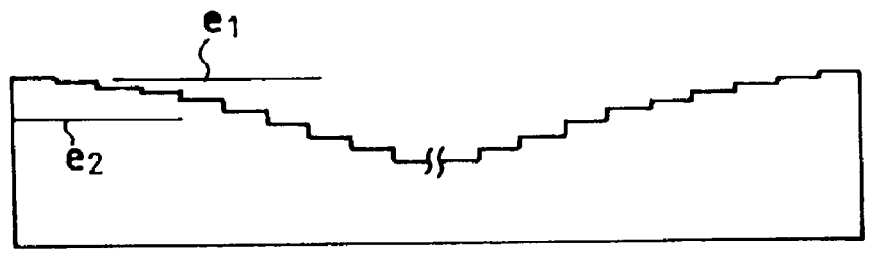
FIG. 10 (B) COEFFICIENT
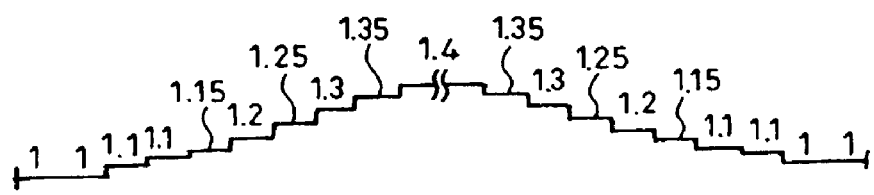

ELECTRONIC ENDOSCOPE ELIMINATING INFLUENCE OF LIGHT DISTRIBUTION IN OPTICAL ZOOMING

BACKGROUND OF THE INVENTION

This application claims the priority of Japanese Patent Applications Nos. 2001-299226 and 2001-299227 and 2001-301804 filed on Sep. 28, 2001 which are incorporated herein by reference.

1. Field of the Invention

The present invention relates to an electronic endoscope having an optical zoom mechanism, and more particularly, to image processing by an electronic endoscope in which a movable lens is driven to bring a tip of a scope close to an object to be observed, and to take an enlarged image.

2. Description of the Related Art

An electronic endoscope takes an image, by an image pickup device such as a CCD (Charge Coupled Device), of an object to be observed, captured via an objective optical system by applying illumination light, and displays the image of the object to be observed on a monitor or the like. Recently, in the electronic endoscope of this type, a movable lens (varifocal type) has been incorporated into the objective optical system, and the movable lens is moved back and forth by a zoom mechanism to optically enlarge the image of the object to be observed. The enlarged image is processed and displayed on the monitor or the like, thus allowing satisfactory observation of details of a site to be observed.

However, in the electronic endoscope having an optical zoom mechanism, there is a problem that varying light distribution prevents an image with even brightness from being obtained in close up photography for obtaining an enlarged image. FIG. 15 shows a state in which a tip of a scope is brought close to the object to be observed, and as shown in this drawing, there are provided, at a tip of a scope 2 for taking an image of an object to be observed 1, illumination windows (lenses) 4a, 4b for applying light guided by a light guide 3, and an observation window (lens) 6 of an objective optical system 5.

At a distance where no zoom function is used, lights $S_1$, $S_2$ from the illumination windows 4a, 4b overlap and are applied to the object to be observed 1, but when the tip 2 is set at a close up distance Da shown in FIG. 15, the lights $S_1$, $S_2$ from the illumination windows 4a, 4b do not overlap, and an area z to which no light is directly applied (a dotted area) appears in the object to be observed 1 as shown in FIG. 16.

In illumination areas of the lights $S_1$, $S_2$, intensity of the light becomes lower from a center of a light spot toward a periphery, and also in the area z, light amount becomes smaller at a position farther from the illumination positions, causing light distribution on the object to be observed. Further, when the zoom function is used, a focusing distance changes depending on power, thus intensity of the illumination light on the object to be observed 1 changes, and the light distribution also changes. In the close up photography using the zoom mechanism, unlike normal photography, there is a problem that the light distribution has a large influence, and an image with even brightness is hard to obtain.

Further, when the movable lens is driven, for example, to an enlargement end (Near end) to bring the tip of a scope 2 extremely close to the object to be observed 1 as shown in FIG. 15, both lights $S_1$, $S_2$ scatter inside the object to be observed 1 (for example, in a mucosa layer) in the area z of the object to be observed 1, to which no light is directly applied in FIG. 16. Thus, there is a problem that an image with redness is formed in taking an image of an object to be observed in vivo by the electronic endoscope.

SUMMARY OF THE INVENTION

The present invention has been achieved in view of the above described problems, and has an object to provide an electronic endoscope having an optical zoom mechanism capable of providing an image with even brightness by eliminating an influence of light distribution, and improving an image with redness at an area to which no light is directly applied in photography of an enlarged image.

To achieve the above described object, an electronic endoscope according to a first aspect of the invention includes: a zoom mechanism, with a movable lens incorporated into an objective optical system, for optically enlarging an image by driving the movable lens; an image signal formation circuit for forming a predetermined image signal based on a signal output from an image pickup device via the objective optical system; and a light distribution correction circuit for multiplying the image signal by a coefficient set in view of the light distribution depending on focusing distances by the movable lens in order to eliminate uneven brightness of an image resulting from the light distribution of varying illumination light in operation of the zoom mechanism.

According to a configuration of the first aspect of the invention, an enlarged image can be obtained by moving the movable lens, for example, forward. A focusing position at this time is recognized by a microcomputer as a drive lens position of the movable lens, and signals of each color, that is, R, G, B signals (or a brightness signal and a color difference signal) are multiplied by a coefficient for eliminating the light distribution set at each lens position. This eliminates unevenness of the illumination light resulting from the varying light distribution depending on enlargement ratios.

In the first aspect of the invention, there may be provided a red component cut filter, placed in a supply line of the illumination light applied to the object to be observed, for cutting a long wavelength side in a red band of the illumination light, and a coefficient in view of light amount change (and light distribution at that time) by the red component cut filter may be multiplied in the light distribution correction circuit. Thus, the red component cut filter cuts the long wavelength side of red light to improve the image with redness (with a tinge of red) of the object to be observed in vivo, and to display mucosa, blood vessels, and other tissue in distinction from one another. When the filter is used, there is an advantage that the light amount becomes insufficient and the light distribution changes, but the insufficiency of the light amount (and light distribution characteristic) is eliminated by coefficient multiplication to improve both the uneven brightness and the redness of the image.

An electronic endoscope according to a second aspect of the invention includes: a zoom mechanism, with a movable lens incorporated into an objective optical system, for optically enlarging an image by driving the movable lens; a signal formation circuit for forming a brightness signal and a color signal based on signals output from an image pickup device via the objective optical system; a coefficient calculation circuit for averaging the brightness signal for a predetermined number of pixels output from the signal formation circuit, comparing averages for the predetermined number of pixels for each horizontal line, and calculating a coefficient for eliminating uneven brightness of an image resulting from light distribution of illumination light; and a multiplier for multiplying the color signal output from the signal formation circuit by the coefficient from the coefficient calculation circuit. Also in the second aspect of the invention, there may be provided a red component cut filter, placed in a supply line of the illumination light applied to the object to be observed, for cutting a long wavelength side in a red band of the illumination light.

According to the second aspect of the invention, the averages for the predetermined number of pixels on the horizontal line can be obtained, and the coefficient for the averages to be constant (even) on the horizontal line is calculated for the predetermined number of pixels. Signals of each color, that is, R, G, B signals (or a brightness signal and a color difference signal) are multiplied by the coefficient, thus eliminating unevenness of illumination light resulting from varying light distribution depending on enlargement ratios.

An electronic endoscope according to a third aspect of the invention includes: a zoom mechanism, with a movable lens incorporated into an objective optical system, for optically enlarging an image by driving the movable lens; a color signal formation circuit for forming a predetermined color signal based on a signal output from an image pickup device via the objective optical system; and a red color reduction circuit for adjusting a predetermined color signal gain formed in the color signal formation circuit and reducing a red color level in an image, when the movable lens is driven to a close up photography area by the zoom mechanism.

According to the third aspect of the invention, when the movable lens is driven, for example, to a Near end, for example, a level of a red (R) color signal obtained via the image pickup device and the color signal formation circuit is reduced in the red color reduction circuit. Thus, redness of an enlarged image in extreme close up photography is improved.

BRIEF DESCRIPTION OF THE DRAWINGS

FIGS. 4(A), 4(B), 4(C), and 4(D) show coefficients stored in a coefficient pattern memory according to the first embodiment, and applied to the distances in FIG. 3;

FIG. 9 shows a light illumination state on an image pickup surface of an image pickup device and the number of pixels that forms a unit for coefficient calculation according to a third embodiment;

FIG. 10(A) shows averages for 32 pixels on a central line Lc in FIG. 9;

FIG. 10(B) shows coefficients for 32 on a central line Lc in FIG. 9;

DETAILED DESCRIPTION OF THE PREFERRED EMBODIMENTS

First Embodiment

Figure 1:
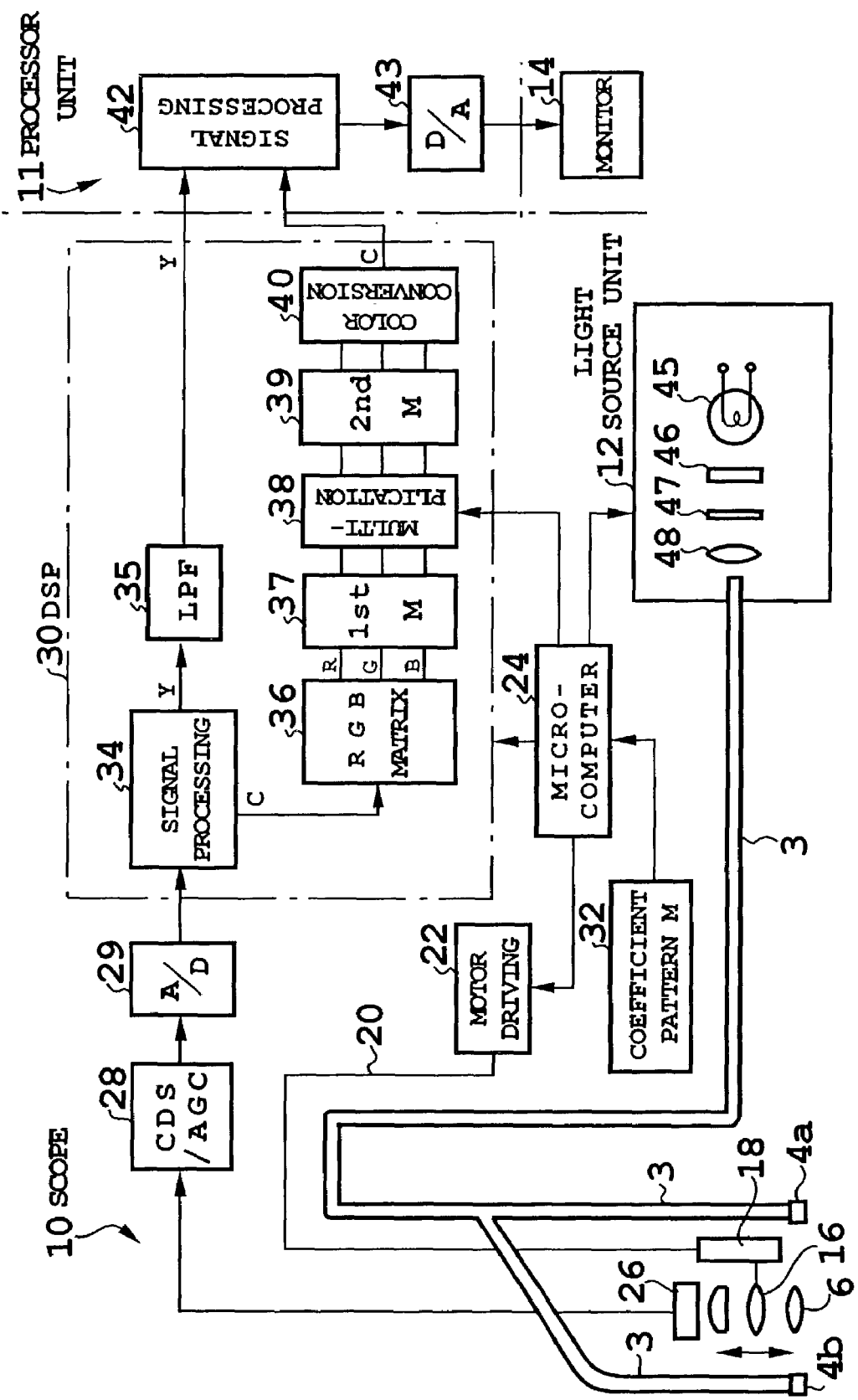
FIG. 1 is a block diagram of a main configuration of an electronic endoscope according to a first embodiment of the invention.

FIG. 1 shows a configuration of an electronic endoscope according to a first embodiment. The electronic endoscope is of a simultaneous type, and includes a scope 10, a processor unit 11, a light source unit 12, and a monitor 14. The endoscope in FIG. 1 includes, at a tip of the scope 10, illumination windows 4a, 4b and an observation window 6, and a light guide 3 guided from the light source unit 12 connects to the illumination windows 4a, 4b.

The observation window 6 constitutes an objective optical system, the objective optical system includes a movable lens 16, and the movable lens 16 is held by and connected to a moving mechanism 18. To the moving mechanism 18, a motor driving unit 22 connects via a rotating linear transfer member 20, and the motor driving unit 22 is controlled by a microcomputer 24. Specifically, based on operation of a zoom switch placed at an operating portion or the like of the scope 10, the microcomputer 24 rotates a motor of the motor driving unit 22, and transfers the rotation to the moving mechanism 18 via the linear transfer member 20, and the moving mechanism 18 converts the rotating motion to linear motion to move the movable lens 16 back and forth. The movable lens 16 is driven and controlled to each position (for example, 256 control positions) from a Far end to a Near end, thus performing optical zooming.

At a rear of the objective optical system including the movable lens 16, a CCD 26 that is an image pickup device is provided, and the CCD 26 captures an image of an object to be observed through color filters (for example, Mg (magenta), G (green), Cy (cyan), and Ye (yellow)) for each pixel. Specifically, light from the light source unit 12 is applied from a tip of the scope 10 via the light guide 3 to the object to be observed, thus an image of the object to be observed is captured by the CCD 26.

After the CCD 26, a CDS (correlated double sampling)/AGC (automatic gain control) circuit 28 is provided, and this CDS/AGC 28 performs correlated double sampling and predetermined amplification processing of an output signal from the CCD 26. After the CDS/AGC 28, a DSP (digital signal processor) 30 is provided via an A/D (analog/digital) converter 29.

In the scope 10, a pattern memory 32 is provided that stores coefficient pattern (table) data corresponding to a drive lens position (focusing distance) of the movable lens 16, and the coefficient pattern is fed to the DSP 30 by control by the microcomputer 24 that recognizes a lens position of the movable lens 16. The DSP 30 includes a signal processing circuit 34 for performing various kinds of processing such as white balance, or gamma correction, and forming a Y (brightness) signal and color difference (C) signals of R (red)–Y and B (blue)–Y, and a low-pass filter (LPF) 35 for passing low frequency of the Y signal. Specifically, in the signal processing circuit 34, the Y signal and the color difference signals of R–Y and B–Y are formed by color conversion calculation from signals obtained through color filters of Mg, G, Cy, Ye of the CCD 26.

Further, there are provided an RGB matrix circuit 36 for converting the color difference signals into R (red), G (green), and B(blue) signals, a first memory 37 for storing the R, G, B signals output from the RGB matrix circuit 36, a multiplier 38 for multiplying each of the R, G, B signals by the coefficient read from the coefficient pattern memory 32, a second memory 39 for storing output from the multiplier 38, and a color conversion circuit 40 for returning the R, G, B signals output from the second memory 39 to the color difference signals of R–Y and B–Y. Specifically, in this embodiment, the Y, C signals are color converted to obtain the R, G, B signals, and the coefficient corresponding to the drive position of the movable lens 16 determined by the microcomputer 24 is read from the pattern memory 32 to multiply each of the R, G, B signals by the coefficient for each pixel.

The processor unit 11 includes a signal processing circuit 42 for inputting the Y signal and the color difference C signal output from the DSP 30, and a D/A converter 43, and in the signal processing circuit 42, various kinds of signal processing for output to the monitor 14 are performed.

Figure 2:
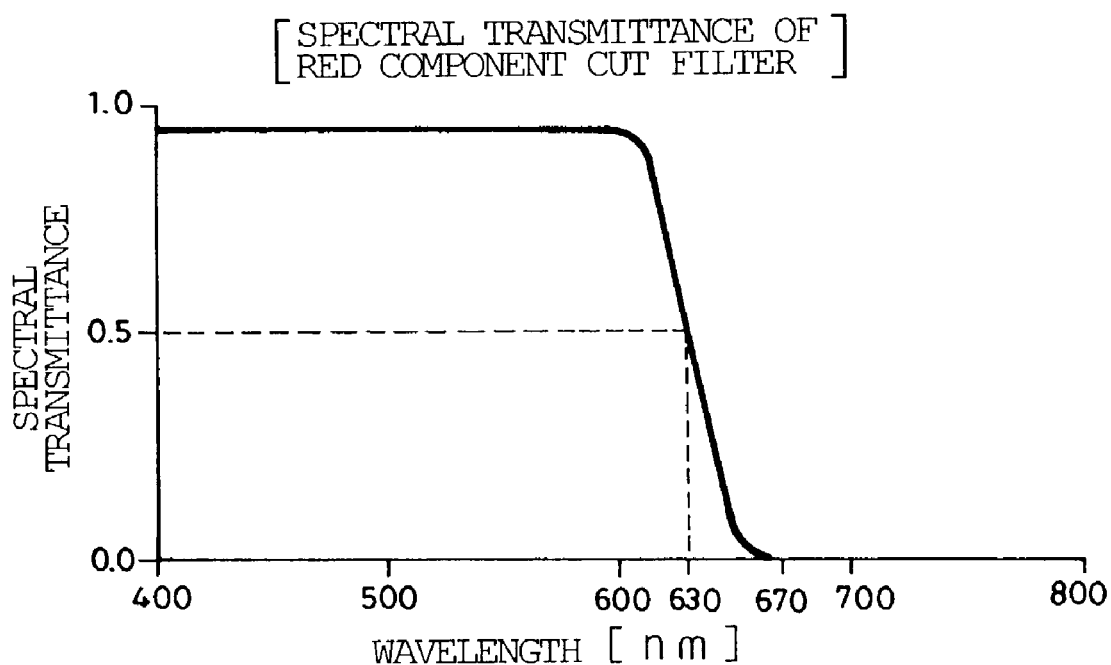
FIG. 2 shows a characteristic of a spectral transmittance of a red component cut filter used in the embodiment.

The light source unit 12 includes a lamp 45, a red component cut filter 46, a light amount aperture 47, and a condenser 48, and light output from the condenser 48 is fed to the light guide 3. FIG. 2 shows a spectral transmittance characteristic of the red component cut filter 46, and the filter 46 has a characteristic that a spectral transmittance becomes half at 630 nm (±10 nm) and zero at 670 nm. As shown in FIG. 2, the red component cut filter 46 cuts more than half of wavelength components of 630 nm and higher in output light from the lamp 45.

The first embodiment is configured as described above, and operation thereof will be described below. First, according to the optical zoom mechanism, operating the zoom switch provided at the operating portion of the scope 10 or the like causes the movable lens 16 to move back and forth, thus providing an optically enlarged image. As the movable lens 16 is moved from the Far position toward the Near position, the focusing position is shifted to a close up side, and a distance between the tip of the scope and the object to be observed becomes extremely short.

On the other hand, light output from the light source unit 12 is applied to the object to be observed via the light guide 3, and when the image of the object to be observed is taken by the CCD 26, the output signal from the CCD 26 is sampled and amplified in the CDS/AGC 28, and fed via the A/D converter 29 to the DSP 30. In the DSP 30, the signal processing circuit 34 performs various kinds of image processing of a video signal to form the Y (brightness) signal and the C (color difference) signal of R–Y and B–Y, and the Y signal is fed to the signal processing circuit 42 via the LPF 35.

Figure 3:
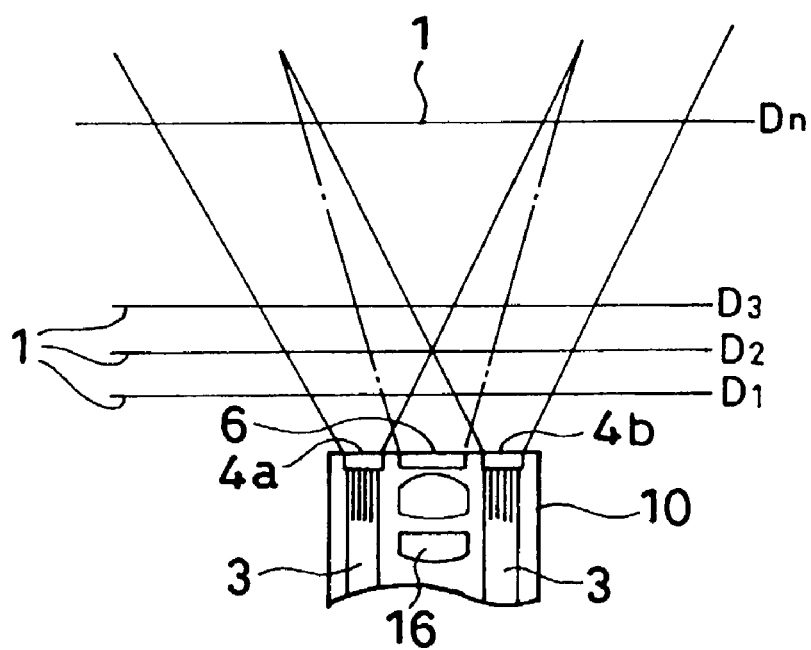
FIG. 3 shows focusing distances in operation of a zoom mechanism according to the embodiment.

The C signal is converted to the R, G, B signals in the RGB matrix 36 and stored in the first memory 37, and the multiplier 38 multiplies the R, G, B signals read from the first memory 37 by the coefficient. As shown in FIG. 3, when the movable lens 16 is driven by the zoom mechanism, and the distances between the tip of the scope 10 and the object to be observed 1, that are focusing distances, are $D_1$, $D_2$, $D_3$, $D_n$, coefficients shown in FIG. 4 are stored in the pattern memory 32.

In FIGS. 4(A) to (D), for example, at the distance $D_1$ in FIG. 4(A), coefficients are set to 1.25 at a central position, 1.18 at edges of illumination areas of lights $S_1$, $S_2$, 1.10 at right and left ends on a central horizontal line Lb, and coefficients are set to 1.28 at a central position, 1.18 at edges of the illumination areas of the lights $S_1$, $S_2$, 1.12 at right and left ends on upper and lower horizontal lines La, Lc. Other coefficients are set as shown in FIGS. 4(B) to 4(D), and for example, all coefficients are 1 at the distance $D_n$ and longer distances (no coefficient calculation is performed). The multiplier 38 multiplies the R, G, B signals by such coefficients.

The output from the multiplier 38 is once stored in the second memory 39, and returned to the C signal in the color conversion circuit 40, and fed to the signal processing circuit 42. In the signal processing circuit 42, performing other kinds of processing and an output processing causes the image of the object to be observed to be displayed on the monitor 14 via the D/A converter 43. This eliminates unevenness of light illumination resulting from varying light distribution depending on focusing distances (power) in the image enlarged by the zoom mechanism. The focusing distances (or enlargement ratios) are displayed on the monitor 14.

Figure 5:
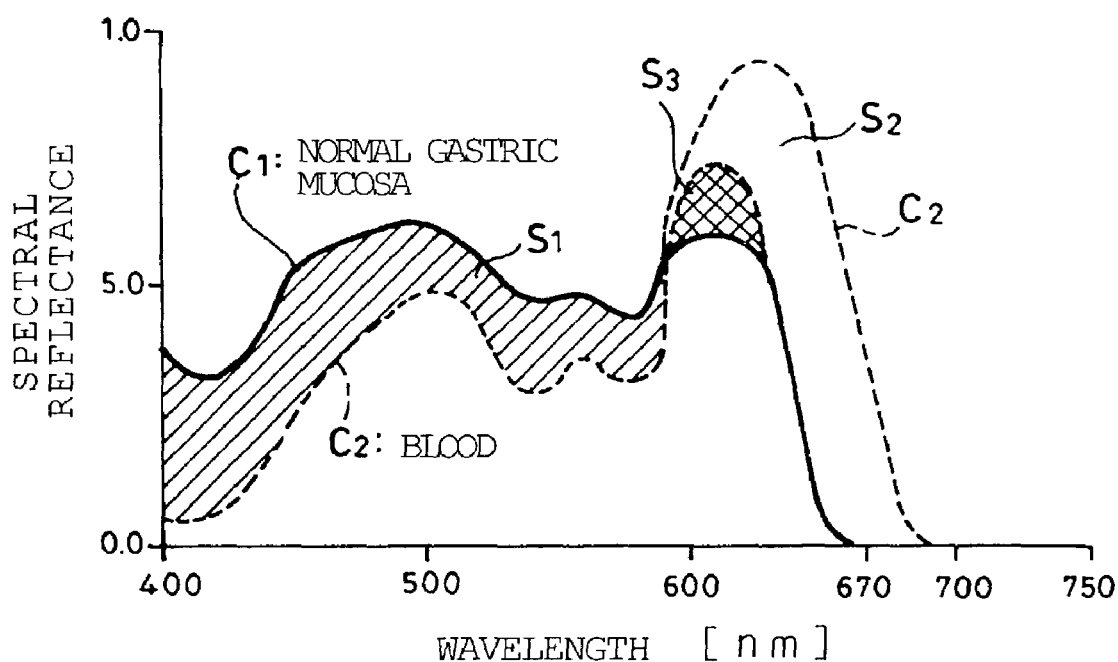
FIG. 5 shows spectral reflectance characteristics of normal gastric mucosa and blood when using a red component cut filter in the embodiment.

FIG. 5 shows spectral reflectances of mucosa and blood when the red component cut filter 46 is placed in the light source unit 12, and in this embodiment, the red component cut filter 46 satisfactorily eliminates the image with redness. In FIG. 5, a spectral reflectance curve of normal gastric mucosa is denoted by $C_1$ (solid line), and a spectral reflectance curve of blood is denoted by $C_2$ (dotted line), and the spectral reflectance curve $C_2$ of the blood significantly increases at wavelengths of 600 nm and higher. An area $S_1$ surrounded by the curves $C_1$ and $C_2$ of wavelengths from 400 nm to near 600 nm shows a component that contributes to contrast between the mucosa, the blood, and other tissue, while an area $S_2$ surrounded by the curves $C_1$ and $C_2$ of wavelengths from near 600 nm and higher shows a component that causes light scattering in a lower layer of the mucosa, and reduces the contrast between the mucosa and the blood.

In this embodiment, providing the red component cut filter 46 causes a wavelength band from near 670 nm and higher to be removed, thus reducing a size of the area $S_2$ to a size of the area $S_3$. This offers advantages of reducing a red component in the image and removing a wavelength component that causes reduction in contrast between the mucosa and the blood, and displaying them in good contrast. When the red component cut filter 46 is used, the light amount becomes insufficient and the light distribution characteristic changes, but the insufficiency of the light amount (and light distribution characteristic) is eliminated by coefficient multiplication to improve both the uneven brightness and the redness of the image.

Second Embodiment

Figure 6:
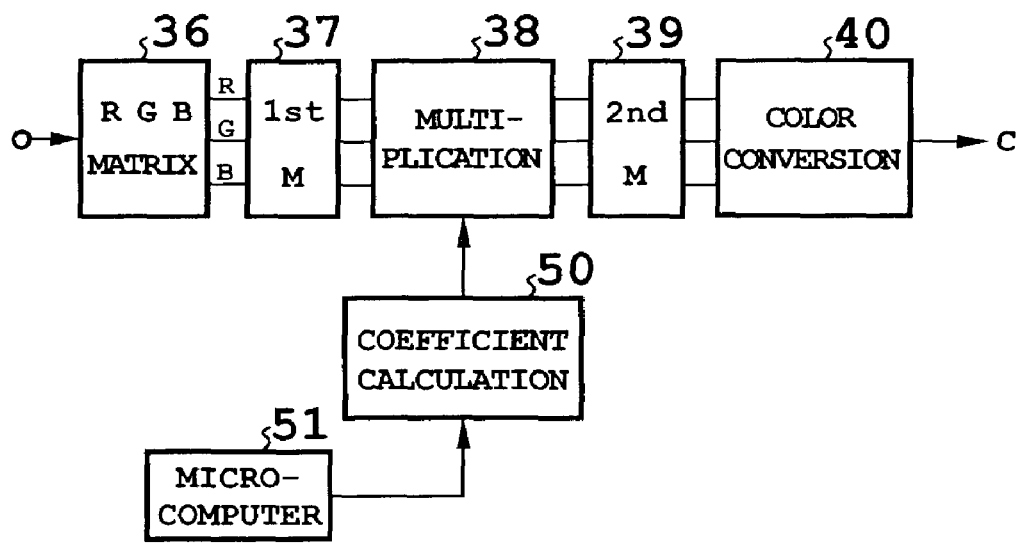
FIG. 6 is a block diagram of a configuration according to a second embodiment.

FIG. 6 shows a configuration of a second embodiment, and in this embodiment, a coefficient for even brightness does not depend on pattern memory, but is calculated in each case. In FIG. 6, in this embodiment, there are provided a coefficient calculation circuit 50 for feeding a coefficient to a multiplier 38, and a microcomputer 51 for controlling the coefficient calculation circuit 50, and the coefficient calculation circuit 50 calculates a coefficient curve (an inversion curve of a light distribution curve) corresponding to a lens position (focusing distance) of a movable lens 18.

Figure 7:
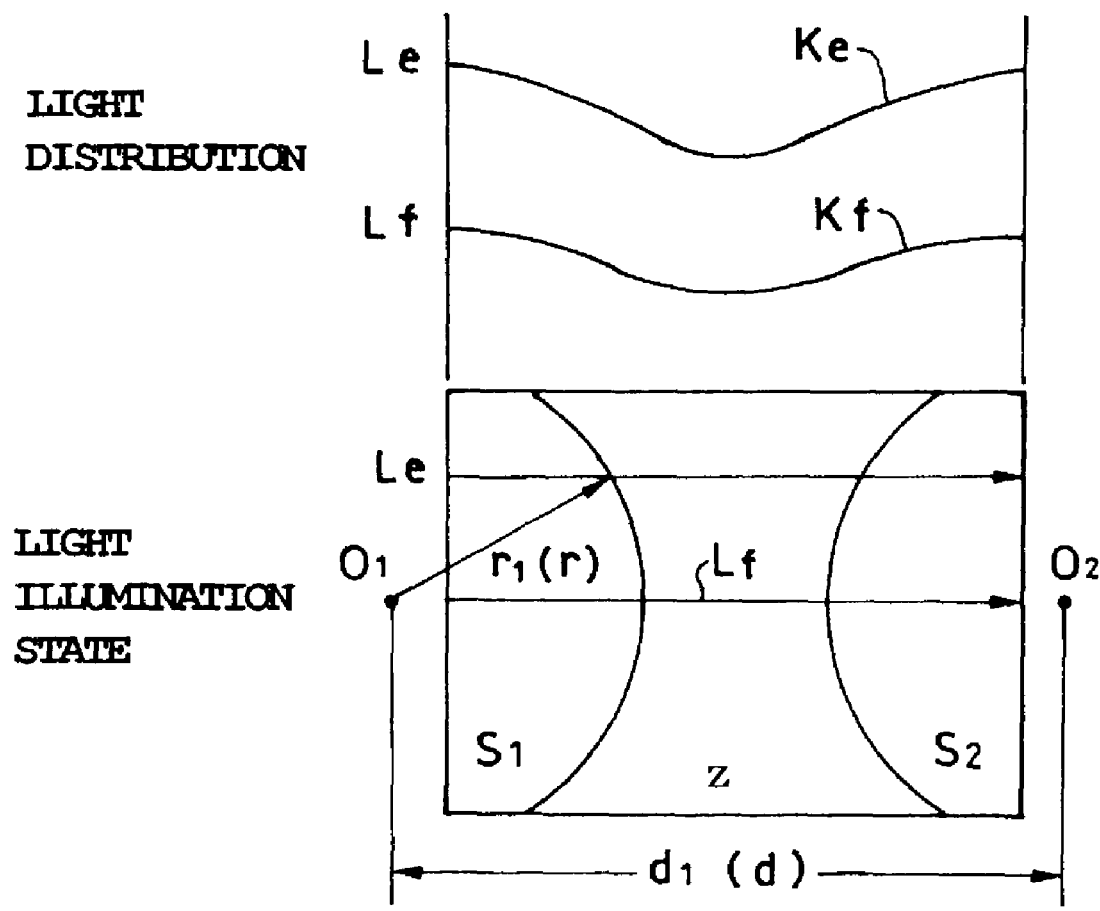
FIG. 7 shows a light illumination state (lower side) and a light distribution curve (upper side) when focusing at a distance $D_1$ in the second embodiment.

FIG. 7 shows a light distribution curve and a light illumination state when focusing at a distance $D_1$ in FIG. 3, and the light distribution curve can be obtained by applying an interval d between central positions $O_1$, $O_2$ in illumination areas of lights $S_1$, $S_2$ determined by the focusing distance, and a radius r of the light illumination area, to an arithmetic equation. For example, values of d, r corresponding to the position of the movable lens 16 and the arithmetic equation are stored in a memory, and when focus is achieved at the distance $D_1$, values of an interval $d_1$ and $r_1$ are used to obtain a curve Kf on a central horizontal line Lf, and a curve Ke on an upper horizontal line Le in the coefficient calculation circuit 50. Inversion signals (coefficient curves) of the curves Ke, Kf are fed to R, G, B signals by a multiplier 38, thus eliminating unevenness of light illumination resulting from varying light distribution depending on enlargement ratios.

The light illumination state in FIG. 7 occurs when the movable lens 16 is at a Near end side, and brightness of the image at this time is uneven. Thus, the illumination areas of the lights $S_1$, $S_2$ and a central portion of a Z area to which no light is directly applied are compared, and when the difference is more than half of a predetermined signal level value in the image, the coefficient calculation is performed, and when the difference is less than half thereof, the coefficient calculation is not performed. The coefficient calculation may be performed manually by a switch separately provided.

In the above described embodiment, the R, G, B signals formed in the RGB matrix circuit 36 is multiplied by the coefficient, but an influence of the light distribution can be similarly improved also by multiplying a Y signal and color difference signals (R-Y and B-Y) output from the signal processing circuit 34 by the coefficient.

As described above, according to the first and second embodiments, the image signal is multiplied by the coefficient set according to the focusing distance by the movable lens and in view of the light distribution of the illumination light, to eliminate the uneven brightness of the image resulting from the varying light distribution in operation of the zoom mechanism, thus providing the image with even brightness without any influence of the light distribution in enlargement photography. Using the red component cut filter allows satisfactory improvement in the image with redness in the area to which no light is applied. This further removes the wavelength component that causes reduction in contrast between the mucosa and the blood, and displays them in good contrast to provide an enlarged image that is easy to observe.

Third Embodiment

Figure 8:
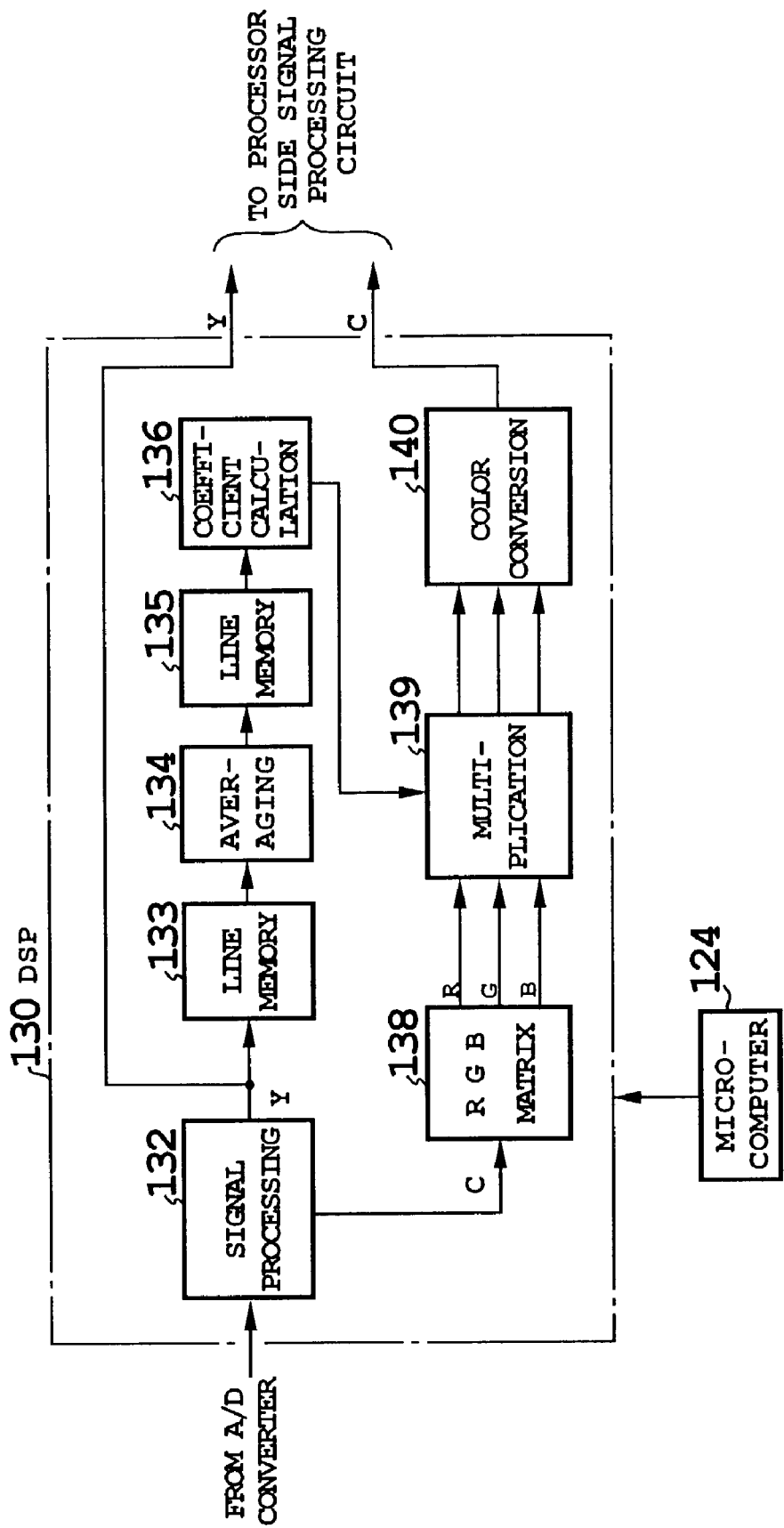
FIG. 8 is a block diagram of a main configuration according to a third embodiment.

FIG. 8 shows a main configuration of an electronic endoscope (scope) according to a third embodiment, and the configuration is similar to the configuration of the first embodiment except for a DSP (digital signal processor) 130 and a microcomputer 124 for controlling the DSP 130. In FIG. 8, the DSP 130 for inputting a video signal from an A/D converter 29 includes a signal processing circuit 132 for performing various kinds of processing such as white balance, or gamma correction, and in the signal processing circuit 132, a Y (brightness) signal and color difference (C) signals of R (red)-Y and B (blue)-Y are formed by color conversion calculation from signals obtained through color filters of Mg, G, Cy, Ye of a CCD 26. There are also provided a line memory 133 for storing the Y signal output from the signal processing circuit 132 for each horizontal line, an averaging circuit 134 for successively determining averages, for example, for 32 pixels (a different number of pixels is acceptable), of a horizontal line signal read from the line memory 133, a line memory 135 for successively storing the averages calculated by the averaging circuit 134, and a coefficient calculation unit 136 for comparing average data of the line memory 135 and calculating coefficients for matching levels of the averages with a predetermined level.

FIG. 9 shows averaged pixels in the CCD 26. In an image pickup surface area 26S in FIG. 9, a screen area of, for example, 768 pixels and 494 lines is set, and on the horizontal line of 768 pixels, averages of the Y signal for 32 pixels are calculated by the averaging circuit 134. Therefore, averages of 24 blocks are obtained, and coefficients for the 24 averages to be constant (even) are determined by the coefficient calculation unit 136.

FIG. 10(A) shows the averages for 32 pixels on the horizontal line in FIG. 9. On a central horizontal line Lc in FIG. 9, a value of the average becomes lower at a position closer to the center, and the average distribution corresponds to the light distribution. Coefficients for matching the averages with a maximum $e_1$ are determined in the coefficient calculation unit 136, and coefficients as shown in FIG. 10(B) are obtained for 32 pixels. In the coefficient calculation, coefficients for matching the averages with an average $e_2$ rather than the maximum $e_1$ may be determined.

There are provided an RGB matrix circuit 138 for converting the color difference signal output from the signal processing circuit 132 into R (red), G (green), and B(blue) signals, a multiplier 139 for multiplying the R, G, B signals output from the RGB matrix circuit 138 by the coefficients output from the coefficient calculation unit 136, and a color conversion circuit 140 for returning the R, G, B signals output from the multiplier 139 to the color difference signals of R-Y, and B-Y. Specifically, the multiplier 139 multiplies each of the R, G, B signals by the coefficients obtained from the Y signal for 32 pixels on the horizontal line, thus eliminating the influence of the light distribution.

The brightness (Y) signal output from the signal processing circuit 132 and the color difference (C) signal output from the color conversion circuit 140 are fed to a signal processing circuit 42 of a process or unit 11. In a light source unit 12, a red component cut filter 46 having a characteristic in FIG. 2 may be provided as described above.

The third embodiment is configured as described above, and operation thereof will be described below. As described above, when operating a zoom switch causes a movable lens 16 to move from a Far position toward a Near position, a focusing position is shifted to a close up side, a tip of a scope is brought close to an object to be observed, and the light distribution of illumination light applied to the object to be observed changes depending on focusing distances.

An image of the object to be observed to which the light is applied is taken by the CCD 26, an output signal from the CCD 26 is fed via the A/D converter 29 to the DSP 130. In the DSP 130, the signal processing circuit 132 performs various kinds of image processing of the video signal to form the Y (brightness) signal and the C (color difference) signal of R-Y and B-Y.

Next, the Y signal is stored in the line memory 133 for each horizontal line, and in the next averaging circuit 134, Y signal data of the horizontal line is averaged for 32 pixels with reference to FIG. 9. Then, 24 averages for 24 blocks (768 pixels) are stored in the line memory 135, and the averages are compared in the next coefficient calculation unit 136, and for example, the coefficients for matching the averages with the maximum $e_1$ in FIG. 10(A) are calculated. This coefficient calculation is performed when a difference between the averages for each block is more than a certain value (threshold value), and for example, the coefficients as shown in FIG. 10(B) are calculated. The coefficients are fed to the multiplier 139.

On the other hand, the C signal output from the signal processing circuit 132 is converted to the R, G, B signals in the RGB matrix 138, and then fed to the multiplier 139, and the multiplier 139 multiplies each of the R, G, B signals by the above described coefficients. Specifically, FIG. 9 shows a state in which illumination lights $S_1$, $S_2$ do not overlap in close up photography and no light is applied to a central portion, and on the central line Lc in FIG. 9, the light distribution is as shown in FIG. 10(A). In this light distribution, the coefficients for matching each average with the maximum $e_1$ become 1.00, 1.00, 1.10, 1.10, 1.15, 1.20, 1.25 . . . for 32 pixels, and the R, G, B signals are multiplied by these coefficients as shown in the figure. This eliminates an influence of variation of the illumination light resulting from the light distribution in FIG. 10(A).

The R, G, B signals output from the multiplier 139 are returned to the C signal in the color conversion circuit 140, and fed to a signal processing circuit 142 in FIG. 1. Thus, the image of the object to be observed is displayed on the monitor 14, and unevenness of light illumination resulting from varying light distribution depending on focusing distances (power) is eliminated in the image enlarged by the zoom mechanism.

In the microcomputer 124, the calculation and the multiplication of the coefficients is not performed when the movable lens 16 is at the Far end in the zoom mechanism, but is started at a lens position when the movable lens 16 is driven from the Far end toward the Near end, or a predetermined lens position (for example, an intermediate lens position). Specifically, an influence of the light distribution of the illumination light on brightness of the image in close up photography in zoom operation is eliminated.

Further, also in the third embodiment, providing the red component cut filter 46 causes a wavelength band from near 670 nm and higher to be removed, thus reducing a size of the area $S_2$ to a size of the area $S_3$ with reference to FIG. 5. This reduces the wavelength component that causes reduction in contrast between the mucosa and the blood, and allows displaying them in good contrast. When the red component cut filter 46 is used, the light amount becomes insufficient and the light distribution characteristic changes, but the insufficiency of the light amount (and light distribution characteristic) is eliminated by the coefficient multiplication to improve both the uneven brightness and the redness of the image.

In the third embodiment, the R, G, B signals formed in the RGB matrix circuit 138 are multiplied by the coefficients, but the influence of the light distribution can be similarly improved by multiplying the color difference signals (R-Y and B-Y) output from the signal processing circuit 132 by the coefficients.

As described above, according to the third embodiment, the brightness signals for a predetermined number of pixels are averaged, and the averages are compared for each horizontal line, the coefficients for the averages to be even are calculated, and the color signal is multiplied by the coefficients for the predetermined number of pixels, thus eliminating the influence of varying light distribution in enlargement photography to provide an image of uniform brightness.

Fourth Embodiment

Figure 11:
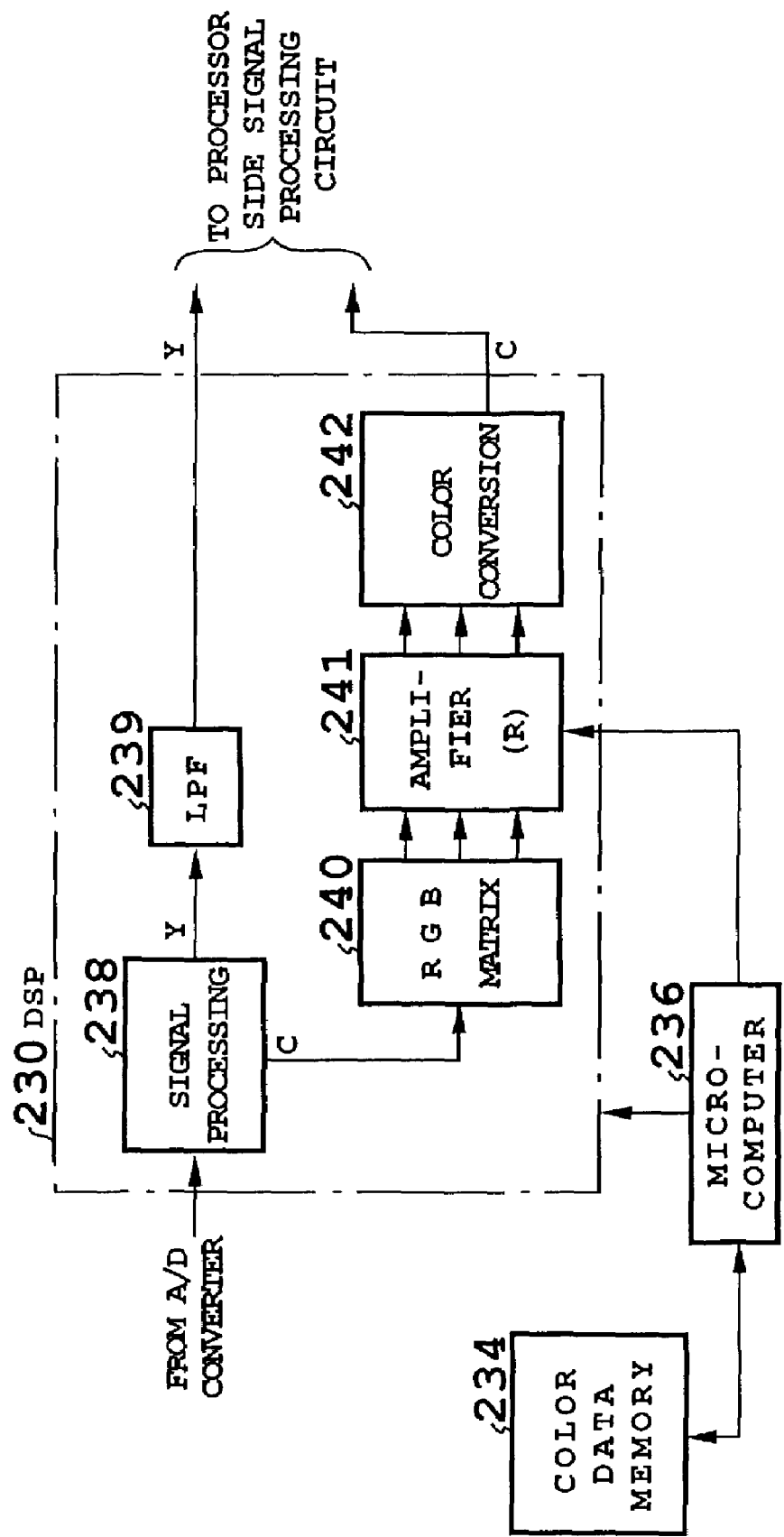
FIG. 11 is a block diagram of a main configuration according to a fourth embodiment.

FIG. 11 shows a main configuration of an electronic endoscope (scope) according to a fourth embodiment, and the configuration is similar to the configuration of the first embodiment except for the configuration in this drawing. In FIG. 11, a scope 10 includes a color data memory 234 for storing gain data for amplifying a standard color signal and gain data for reducing an R (red) signal level in operation to a close up photography area (in this embodiment, in extreme close up photography (in Near end driving)), or the like, and a microcomputer 236 for collectively controlling the entire parts.

A DSP 230 for inputting a video signal from an A/D converter 29 includes a signal processing circuit 238 for performing various kinds of processing such as white balance, or gamma correction, and forming a Y (brightness) signal and color difference (C) signals of R (red)-Y and B (blue)-Y, and a low-pass filter (LPF) 239 for passing low frequency of the Y signal. Specifically, in the signal processing circuit 238, the Y signal and the color difference signals of R-Y and B-Y are formed by color conversion calculation from signals obtained through color filters of Mg, G, Cy, Ye of a CCD 26.

Figure 12:
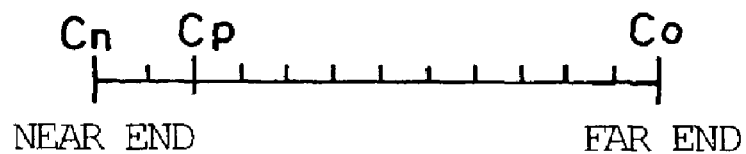
FIG. 12 shows a position in which a movable lens of an optical zoom mechanism according to the fourth embodiment is driven.

Further, there are provided an RGB matrix circuit 240 for converting the color difference (C) signals into R (red), G (green), and B(blue) signals, an amplifier 241 for reducing a level of the R signal only based on an R gain in extreme close up photography stored in the color data memory 234, and a color conversion circuit 242 for returning the R, G, B signals to the color difference signals of R-Y, and B-Y. Specifically, in this embodiment, the Y and C signals are color converted to obtain the R signal, and when the microcomputer 236 determines that a movable lens 16 is at a Near end (CN) in FIG. 12, the R signal is amplified by the R gain in the extreme close up photography, and for example, the signal level is reduced to ½. The brightness (Y) signal and the color difference (C) signals output from the DSP 230 are fed to a signal processing circuit 42 in a processor unit 11.

Figure 13:
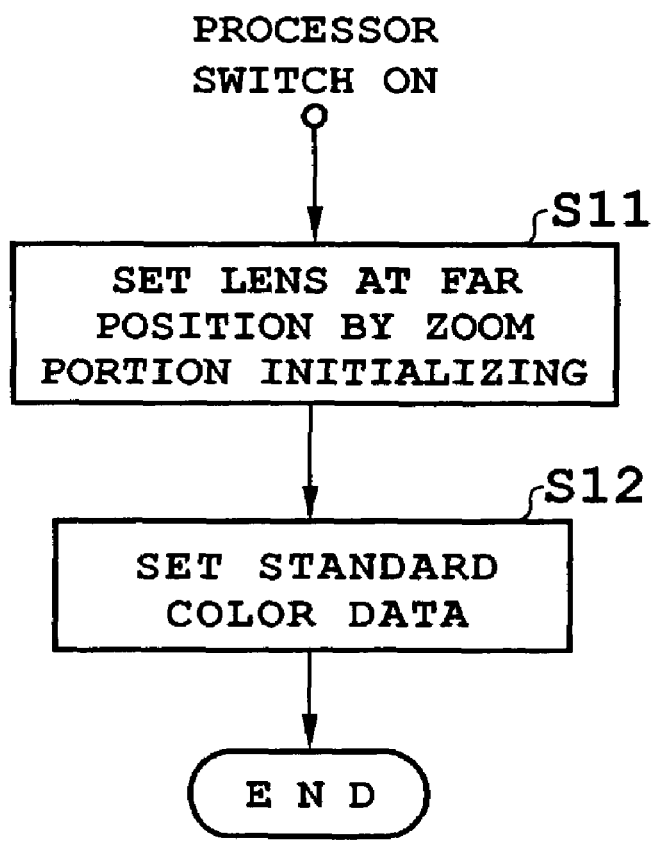
FIG. 13 is a flowchart of operation at switch on of a microcomputer according to the fourth embodiment.

The fourth embodiment is configured as described above, and operation thereof will be described below. FIG. 13 shows operation by the microcomputer 236 at switch on, and when the power switch of the processor unit 11 is turned on, operation setting is initialized. In Step S11, the movable lens 16 is driven to a Far position by zoom portion initializing, and in next Step S12, standard color data is set. Then, when an image of an object to be observed to which light from a tip of a scope 10 is applied is taken by the CCD 26, an output signal from the CCD 26 is fed via a CDS/AGC 28 and an A/D converter 29 to a DSP 130 as digital signals.

In the DSP 130, the signal processing circuit 238 performs various kinds of image processing of a video signal to form the Y (brightness) signal and the C (color difference) signals of R-Y and B-Y, and the Y signal is fed to the processor unit 11 via the LPF 239. On the other hand, the C signal is fed to the process or unit 11 via the RGB matrix 240, the amplifier 241, and the color conversion circuit 242, but the R, G, B signals are amplified by the amplifier 141 based on standard color data other than in the extreme close up photography. In such an endoscope, operating a zoom switch placed at an operating portion or the like causes the movable lens 16 to move toward the Near end Cn in FIG. 12, thus providing an enlarged image focusing on the object to be observed to which the tip of the scope is brought close.

Figure 14:
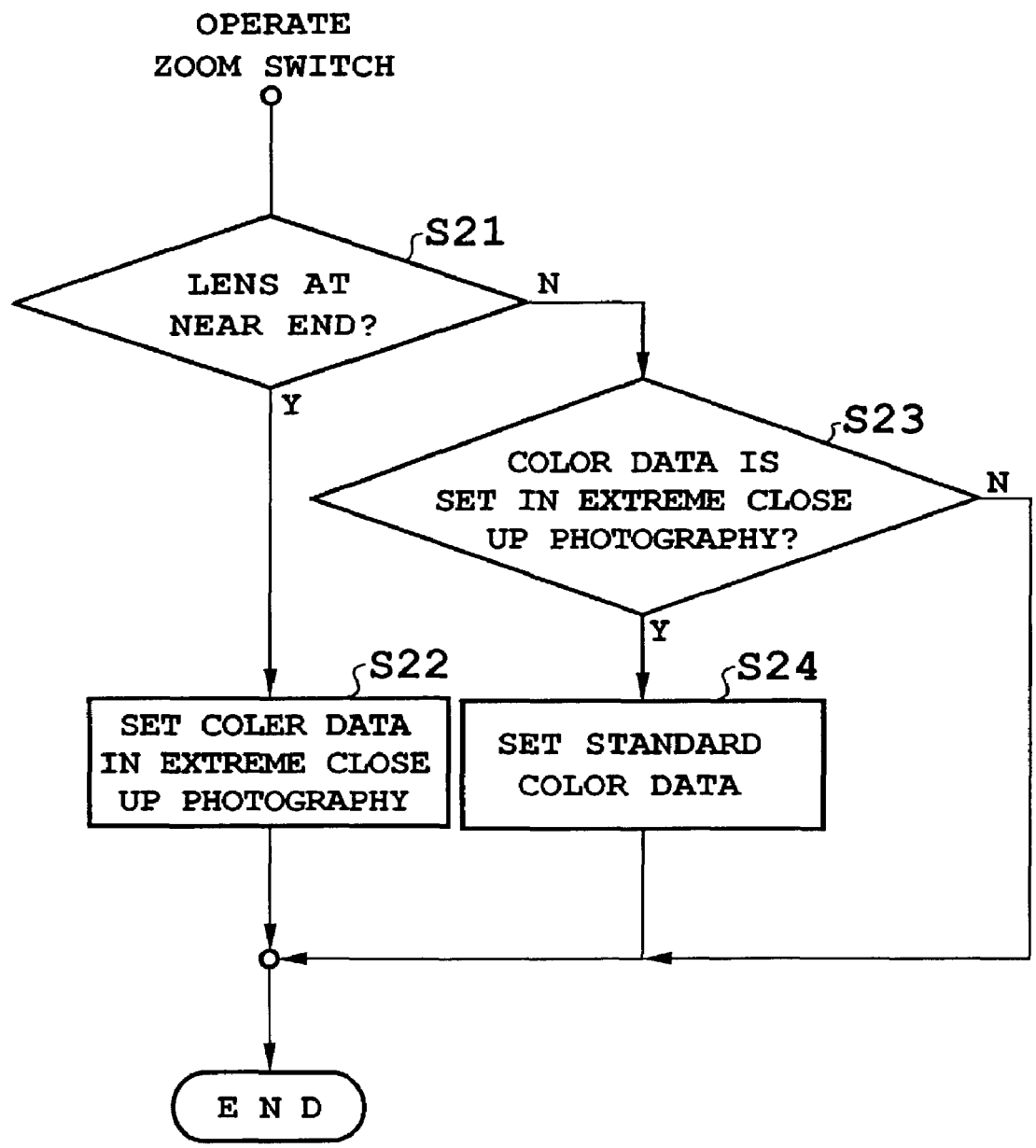
FIG. 14 is a flowchart of operation in zoom switch operation of the microcomputer according to the fourth embodiment.
Figure 15:
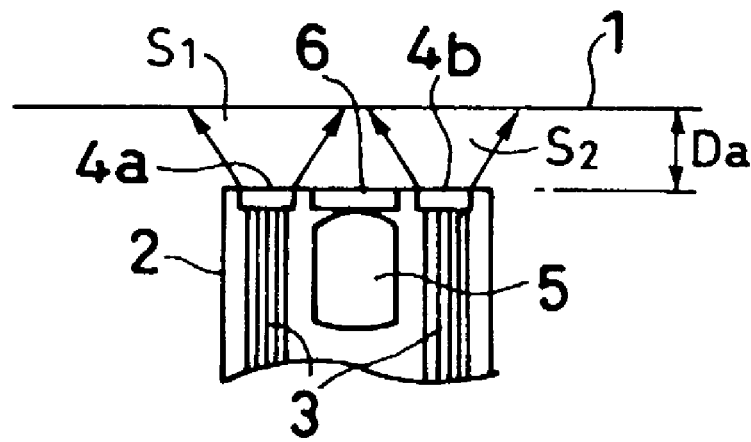
FIG. 15 shows a light illumination state when a tip of a scope is brought close to an object to be observed.
Figure 16:
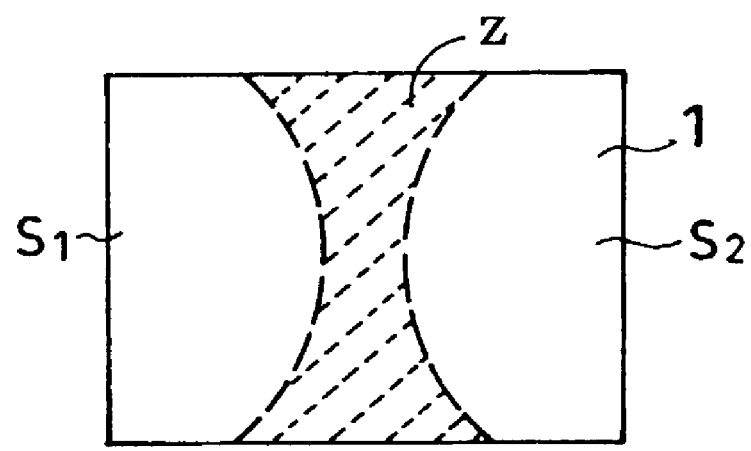
FIG. 16 shows a display state of the object to be observed in FIG. 15.

FIG. 14 shows operation of the microcomputer 236 relating to the operation of the zoom switch. When the zoom switch is operated (turned on), it is determined whether the movable lens 16 is at the Near end in Step S21, and when Y (YES), color data in the extreme close up photography is set in Step S23. For the color data in the extreme close up photography, an amplification ratio of the R signal only is ½ of, for example, the standard color data. Thus, in the extreme close up photography in which the movable lens 16 is set to the Near end Cn in FIG. 12, an image with half the R signal level as compared with other photography is formed. This eliminates a red tone of the image shown in FIG. 15, and improves the image with redness.

Step S21 in FIG. 14, when N (NO), that is, when the movable lens 16 is not at the Near end (Cn), it is determined that the color data in the extreme close up photography is now set in Step S23, and when Y, the standard color data is set in Step S24. Thus, when the movable lens 16 is driven to other than the Near end by the zoom switch, the color data in the extreme close up photography is switched to the standard color data to perform standard image processing.

In the fourth embodiment, the R signal level of the R, G, B signals is reduced in the extreme close up photography, but similar advantages can be obtained by reducing the R–Y signal level of the color difference signal. The red level is reduced when the movable lens 16 is driven to the Near end (Cn), but a reduction start position of the red level may extend to a position of Cp (close up photography are) before the Near end Cn in FIG. 12. Further, the R, G, B signals can be directly formed rather than conversion from the color difference signals in the DSP 130, and in such a case, the amplification of the R signal by the R gain may be performed.

As described above, according to the fourth embodiment, the image with redness can be improved that occurs in enlarged image photography in which the tip of the scope is brought extremely close to the object to be observed, thus providing a close up enlarged image that is easy to observe.

What is claimed is:

1. An electronic endoscope comprising:
   a zoom mechanism having a movable lens incorporated into an objective optical system thereof for optically enlarging an image by driving the movable lens;
   an image signal formation circuit for forming a predetermined image signal based on a signal output from an image pickup device via said objective optical system; and
   a light distribution correction circuit for multiplying said image signal by a coefficient set in view of said light distribution depending on focusing distances by said movable lens in order to eliminate uneven brightness of an image resulting from the light distribution of varying illumination light in operation of said zoom mechanism.

2. The electronic endoscope according to claim 1, further comprising a red component cut filter, placed in a supply line of the illumination light applied to the object to be observed, for cutting a long wavelength side in a red band of the illumination light, wherein a coefficient in view of light amount change by the red component cut filter is multiplied in said light distribution correction circuit.

3. The electronic endoscope according to claim 1, further comprising a coefficient calculation circuit for calculating said coefficient in view of the light distribution.

4. The electronic endoscope according to claim 1, wherein said light distribution correction circuit performs coefficient calculation when brightness levels of direct light illumination areas and an area other than those areas are more than predetermined values.

5. An electronic endoscope comprising:
   a zoom mechanism having a movable lens incorporated into an objective optical system thereof for optically enlarging an image by driving the movable lens;
   a signal formation circuit for forming a brightness signal and a color signal based on a signal output from an image pickup device via said objective optical system;
   a coefficient calculation circuit for averaging the brightness signal for a predetermined number of pixels output from the signal formation circuit, comparing averages for the predetermined number of pixels for each horizontal line, and calculating a coefficient for eliminating uneven brightness of an image resulting from light distribution of illumination light; and
   a multiplier for multiplying the color signal output from said signal formation circuit by the coefficient from the coefficient calculation circuit.

6. The electronic endoscope according to claim 5, further comprising a red component cut filter, placed in a supply line of the illumination light applied to the object to be observed, for cutting a long wavelength side in a red band of the illumination light.

7. The electronic endoscope according to claim 5, said coefficient calculation circuit performs coefficient calculation when a difference between the averages for each block on the horizontal line is more than a predetermined threshold value.

8. An electronic endoscope having an optical zooming mechanism comprising:
   a zoom mechanism having a movable lens incorporated into an objective optical system thereof for optically enlarging an image by driving the movable lens;
   a color signal formation circuit for forming a predetermined color signal based on a signal output from an image pickup device via said objective optical system; and
   a red color reduction circuit for adjusting a predetermined color signal gain formed in said color signal formation circuit and reducing a red color level in an image, when said movable lens is driven to a close up photography area by said zoom mechanism.

* * * * *